US011179559B2

(12) United States Patent
Hansen

(10) Patent No.: US 11,179,559 B2
(45) Date of Patent: Nov. 23, 2021

(54) RESONANT POWER TRANSFER SYSTEMS WITH COMMUNICATIONS

(71) Applicant: TC1 LLC, St. Paul, MN (US)

(72) Inventor: John Freddy Hansen, Pleasanton, CA (US)

(73) Assignee: TC1 LLC, St. Paul, MN (US)

( * ) Notice: Subject to any disclaimer, the term of this patent is extended or adjusted under 35 U.S.C. 154(b) by 0 days.

(21) Appl. No.: 16/879,109

(22) Filed: May 20, 2020

(65) Prior Publication Data

US 2020/0276371 A1    Sep. 3, 2020

Related U.S. Application Data

(63) Continuation of application No. 15/032,290, filed as application No. PCT/US2014/064951 on Nov. 11, 2014, now Pat. No. 10,695,476.

(Continued)

(51) Int. Cl.
*A61M 1/12* (2006.01)
*A61B 5/00* (2006.01)
(Continued)

(52) U.S. Cl.
CPC ......... *A61M 60/871* (2021.01); *A61B 5/0031* (2013.01); *A61M 60/50* (2021.01);
(Continued)

(58) Field of Classification Search
CPC .............. A61M 1/127; A61M 1/1086; A61M 2205/8243; A61M 1/12; A61B 5/0031;
(Continued)

(56) References Cited

U.S. PATENT DOCUMENTS 4,041,955 A    8/1977 Kelly et al.
4,352,960 A    10/1982 Dormer et al.
(Continued)

FOREIGN PATENT DOCUMENTS

DE    202012000166 U1    6/2013
DE    102012201073 A1    7/2013
(Continued)

OTHER PUBLICATIONS

Bonde et al.; Promise of unrestricted mobility with innovative, portable wireless powering of a mechanical circulatory assist device; American Association for Thoracic Surgery; © 2012; 2 pgs.; retrieved Mar. 12, 2014 from the internet: http://aats.org/annualmeeting/Abstracts/2012/T8.cgi.
(Continued)

*Primary Examiner* — Hal Kaplan
*Assistant Examiner* — Thai H Tran
(74) *Attorney, Agent, or Firm* — Armstrong Teasdale LLP

(57) ABSTRACT

Methods and apparatus for wireless power transfer and communications are provided. In one embodiment, a wireless power transfer system comprises an external transmit resonator configured to transmit wireless power, an implantable receive resonator configured to receive the transmitted wireless power from the transmit resonator, and a user interface device comprising a resonant coil circuit, the resonant coil circuit being configured to receive magnetic communication signals from the transmit resonator or the receive resonator and to display information relating to the magnetic communication signals to a user of the user interface device.

13 Claims, 6 Drawing Sheets

Related U.S. Application Data

(60) Provisional application No. 61/902,692, filed on Nov. 11, 2013.

(51) Int. Cl.
| | | |
|---|---|---|
| *A61M 1/10* | (2006.01) | |
| *H02J 50/12* | (2016.01) | |
| *H02J 50/80* | (2016.01) | |
| *A61M 60/871* | (2021.01) | |
| *A61M 60/50* | (2021.01) | |
| *H02J 7/00* | (2006.01) | |
| *A61M 60/122* | (2021.01) | |

(52) U.S. Cl.
CPC .............. *H02J 50/12* (2016.02); *H02J 50/80* (2016.02); *A61B 2560/0219* (2013.01); *A61M 60/122* (2021.01); *A61M 2205/8243* (2013.01); *H02J 7/0047* (2013.01); *H02J 7/0049* (2020.01)

(58) Field of Classification Search
CPC .. A61B 2560/0219; H02J 50/80; H02J 50/12; H02J 7/0049; H02J 7/0047
USPC ........................................... 307/104; 320/108
See application file for complete search history.

(56) References Cited

U.S. PATENT DOCUMENTS

| | | |
|---|---|---|
| 4,561,443 A | 12/1985 | Hogrefe et al. |
| 4,561,444 A | 12/1985 | Livingston et al. |
| 4,630,615 A | 12/1986 | Yomtov |
| 4,679,560 A | 7/1987 | Galbraith |
| 4,726,378 A | 2/1988 | Kaplan |
| 4,736,747 A | 4/1988 | Drake |
| 4,924,171 A | 5/1990 | Baba et al. |
| 4,945,305 A | 7/1990 | Blood |
| 5,070,223 A | 12/1991 | Colasante |
| 5,346,458 A | 9/1994 | Affeld |
| 5,350,413 A | 9/1994 | Miller et al. |
| 5,432,786 A * | 7/1995 | Kawada .................... H04L 5/06 329/304 |
| 5,569,156 A | 10/1996 | Mussivand |
| 5,630,836 A | 5/1997 | Prem et al. |
| 5,690,693 A | 11/1997 | Wang et al. |
| 5,702,431 A | 12/1997 | Wang et al. |
| 5,755,748 A | 5/1998 | Borza |
| 5,771,438 A | 6/1998 | Palermo et al. |
| 5,831,248 A | 11/1998 | Hojyo et al. |
| 5,948,006 A | 9/1999 | Mann |
| 6,123,726 A | 9/2000 | Mori et al. |
| 6,149,683 A | 11/2000 | Lancisi et al. |
| 6,212,430 B1 | 4/2001 | Kung |
| 6,296,533 B1 | 10/2001 | Grubbs et al. |
| 6,312,338 B1 | 11/2001 | Sato et al. |
| 6,320,354 B1 | 11/2001 | Sengupta et al. |
| 6,324,431 B1 | 11/2001 | Zarinetchi et al. |
| 6,327,504 B1 | 12/2001 | Dolgin et al. |
| 6,389,318 B1 | 5/2002 | Zarinetchi et al. |
| 6,400,991 B1 | 6/2002 | Kung |
| 6,442,434 B1 | 8/2002 | Zarinetchi et al. |
| 6,451,055 B1 | 9/2002 | Weiss |
| 6,458,164 B1 | 10/2002 | Weiss |
| 6,478,820 B1 | 11/2002 | Weiss |
| 6,553,263 B1 | 4/2003 | Meadows et al. |
| 6,579,315 B1 | 6/2003 | Weiss |
| 6,591,139 B2 | 7/2003 | Loftin et al. |
| 6,605,032 B2 | 8/2003 | Benkowski et al. |
| 6,647,298 B2 | 11/2003 | Abrahamson et al. |
| 6,650,213 B1 | 11/2003 | Sakurai et al. |
| 6,723,039 B2 | 4/2004 | French et al. |
| 6,772,011 B2 | 8/2004 | Dolgin |
| 6,801,807 B2 | 10/2004 | Abrahamson |
| 6,810,289 B1 | 10/2004 | Shaquer |
| 6,850,803 B1 | 2/2005 | Jimenez et al. |
| 6,894,456 B2 | 5/2005 | Tsukamoto et al. |
| 6,895,281 B1 | 5/2005 | Amundson et al. |
| 6,949,065 B2 | 9/2005 | Sporer et al. |
| 6,960,968 B2 | 11/2005 | Odenaal et al. |
| 6,967,621 B1 | 11/2005 | Cadotte, Jr. et al. |
| 6,985,773 B2 | 1/2006 | Von Arx et al. |
| 7,015,769 B2 | 3/2006 | Schulman et al. |
| 7,107,103 B2 | 9/2006 | Schulman et al. |
| 7,126,310 B1 | 10/2006 | Barron |
| 7,225,032 B2 | 5/2007 | Schmeling et al. |
| 7,246,040 B2 | 7/2007 | Borg et al. |
| 7,286,880 B2 | 10/2007 | Olson et al. |
| 7,428,438 B2 | 9/2008 | Parramon et al. |
| 7,471,986 B2 | 12/2008 | Hatlestad |
| 7,496,733 B2 | 2/2009 | Altman et al. |
| 7,505,816 B2 | 3/2009 | Schmeling et al. |
| 7,515,012 B2 | 4/2009 | Schulman et al. |
| 7,522,878 B2 | 4/2009 | Baarman |
| 7,532,901 B1 | 5/2009 | LaFranchise et al. |
| 7,565,187 B1 | 7/2009 | Dynok et al. |
| 7,571,007 B2 | 8/2009 | Erickson et al. |
| 7,574,173 B2 | 8/2009 | Terranova et al. |
| 7,587,241 B2 | 9/2009 | Parramon et al. |
| 7,599,743 B2 | 10/2009 | Hassler et al. |
| 7,650,187 B2 | 1/2010 | Gruber et al. |
| 7,650,192 B2 | 1/2010 | Wahlstrand |
| 7,711,433 B2 | 5/2010 | Davis et al. |
| 7,720,546 B2 | 5/2010 | Ginggen et al. |
| 7,741,734 B2 | 6/2010 | Joannopoulos et al. |
| 7,761,164 B2 | 7/2010 | Verhoef et al. |
| 7,774,069 B2 | 8/2010 | Olson et al. |
| 7,782,190 B1 | 8/2010 | Martin et al. |
| 7,805,200 B2 | 9/2010 | Kast et al. |
| 7,812,481 B2 | 10/2010 | Iisaka et al. |
| 7,818,036 B2 | 10/2010 | Lair et al. |
| 7,818,037 B2 | 10/2010 | Lair et al. |
| 7,825,543 B2 | 11/2010 | Karalis et al. |
| 7,830,114 B2 | 11/2010 | Reed |
| 7,865,245 B2 | 1/2011 | Torgerson et al. |
| 7,872,367 B2 | 1/2011 | Recksiek et al. |
| 7,904,170 B2 | 3/2011 | Harding |
| 7,932,696 B2 | 4/2011 | Peterson et al. |
| 7,962,222 B2 | 6/2011 | He et al. |
| RE42,682 E | 9/2011 | Barreras et al. |
| 8,076,801 B2 | 12/2011 | Karalis et al. |
| 8,081,925 B2 | 12/2011 | Parramon et al. |
| 8,096,954 B2 | 1/2012 | Stahmann et al. |
| 8,140,168 B2 | 3/2012 | Olson et al. |
| 8,150,529 B2 | 4/2012 | Snell et al. |
| 8,165,694 B2 | 4/2012 | Carbanaru et al. |
| 8,185,212 B2 | 5/2012 | Carbunaru et al. |
| 8,193,766 B2 | 6/2012 | Rondoni et al. |
| 8,203,434 B2 | 6/2012 | Yoshida |
| 8,244,367 B2 | 8/2012 | Wahlstrand et al. |
| 8,247,926 B2 | 8/2012 | Issa et al. |
| 8,258,653 B2 | 9/2012 | Kitamura et al. |
| 8,265,770 B2 | 9/2012 | Toy et al. |
| 8,278,784 B2 | 10/2012 | Cook et al. |
| 8,292,052 B2 | 10/2012 | Bohori et al. |
| 8,299,652 B2 | 10/2012 | Smith et al. |
| 8,301,079 B2 | 10/2012 | Baarman |
| 8,319,473 B2 | 11/2012 | Choi et al. |
| 8,362,742 B2 | 1/2013 | Kallmyer |
| 8,373,310 B2 | 2/2013 | Baarman et al. |
| 8,378,522 B2 | 2/2013 | Cook et al. |
| 8,378,523 B2 | 2/2013 | Cook et al. |
| 8,463,395 B2 | 6/2013 | Forsell |
| 8,489,200 B2 | 7/2013 | Zarinetchi et al. |
| 8,551,163 B2 | 10/2013 | Aber et al. |
| 8,562,508 B2 | 10/2013 | Dague et al. |
| 8,581,793 B2 | 11/2013 | Carr |
| 8,587,154 B2 | 11/2013 | Fells et al. |
| 8,620,447 B2 | 12/2013 | D'Ambrosio et al. |
| 8,628,460 B2 | 1/2014 | Yomtov et al. |
| 8,629,578 B2 | 1/2014 | Kurs et al. |
| 8,668,473 B2 | 3/2014 | Larose et al. |
| 8,694,117 B2 | 4/2014 | Aghassian et al. |
| 8,810,071 B2 | 8/2014 | Sauerlaender et al. |

(56) References Cited

U.S. PATENT DOCUMENTS

| | | |
|---|---|---|
| 8,884,468 B2 | 11/2014 | Lemmens et al. |
| 8,909,351 B2 | 12/2014 | Dinsmoor et al. |
| 8,971,958 B2 | 3/2015 | Frikart et al. |
| 9,002,468 B2 | 4/2015 | Shea et al. |
| 9,106,083 B2 | 8/2015 | Partovi |
| 9,192,704 B2 | 11/2015 | Yomtov et al. |
| 9,302,093 B2 | 4/2016 | Mashiach |
| 9,515,494 B2 | 12/2016 | Kurs et al. |
| 9,515,495 B2 | 12/2016 | Kurs et al. |
| 9,560,787 B2 | 1/2017 | Kallmyer et al. |
| 2002/0032472 A1 | 3/2002 | Zarinetchi |
| 2002/0038138 A1 | 3/2002 | Zarinetchi et al. |
| 2002/0087204 A1 | 7/2002 | Kung et al. |
| 2002/0093456 A1 | 7/2002 | Sawamura et al. |
| 2003/0026269 A1* | 2/2003 | Paryani ............. H04L 65/1026 370/401 |
| 2003/0078634 A1 | 4/2003 | Schulman et al. |
| 2003/0171792 A1 | 9/2003 | Zarinetchi et al. |
| 2004/0098068 A1 | 5/2004 | Carbunaru |
| 2004/0138725 A1 | 7/2004 | Forsell |
| 2004/0256146 A1 | 12/2004 | Frericks |
| 2005/0006083 A1 | 1/2005 | Chen et al. |
| 2005/0075682 A1 | 4/2005 | Schulman |
| 2005/0075694 A1 | 4/2005 | Schmeling |
| 2005/0090883 A1 | 4/2005 | Westlund et al. |
| 2005/0288743 A1 | 12/2005 | Ahn et al. |
| 2006/0199997 A1 | 9/2006 | Hassler et al. |
| 2006/0271129 A1 | 11/2006 | Tai et al. |
| 2007/0096686 A1 | 5/2007 | Jimenez et al. |
| 2007/0123948 A1 | 5/2007 | Dal Molin |
| 2007/0142696 A1 | 6/2007 | Crosby et al. |
| 2007/0191706 A1 | 8/2007 | Calderon et al. |
| 2008/0009198 A1 | 1/2008 | Marino |
| 2008/0027293 A1 | 1/2008 | Vodermayer et al. |
| 2008/0054638 A1 | 3/2008 | Greene et al. |
| 2008/0092911 A1 | 4/2008 | Schulman |
| 2008/0100294 A1 | 5/2008 | Rohling et al. |
| 2008/0149736 A1 | 6/2008 | Kim et al. |
| 2008/0167531 A1 | 7/2008 | McDermott |
| 2008/0194912 A1 | 8/2008 | Trovato |
| 2008/0211320 A1 | 9/2008 | Cook et al. |
| 2009/0018616 A1 | 1/2009 | Quick et al. |
| 2009/0051224 A1 | 2/2009 | Cook et al. |
| 2009/0072628 A1 | 3/2009 | Cook et al. |
| 2009/0081943 A1 | 3/2009 | Dobyns et al. |
| 2009/0174264 A1 | 7/2009 | Onishi et al. |
| 2009/0212736 A1 | 8/2009 | Baarman et al. |
| 2009/0226328 A1 | 9/2009 | Morello |
| 2009/0264069 A1 | 10/2009 | Yamasuge |
| 2009/0270679 A1 | 10/2009 | Hoeg et al. |
| 2009/0284220 A1 | 11/2009 | Toncich et al. |
| 2009/0292341 A1 | 11/2009 | Parramon |
| 2010/0019985 A1 | 1/2010 | Bashyam et al. |
| 2010/0033021 A1 | 2/2010 | Bennett |
| 2010/0035453 A1 | 2/2010 | Tronnes et al. |
| 2010/0039234 A1 | 2/2010 | Soliven |
| 2010/0045114 A1 | 2/2010 | Sample et al. |
| 2010/0063347 A1 | 3/2010 | Yomtov et al. |
| 2010/0066305 A1 | 3/2010 | Takahashi et al. |
| 2010/0069992 A1 | 3/2010 | Aghassian et al. |
| 2010/0102639 A1 | 4/2010 | Joannopoulos et al. |
| 2010/0109958 A1 | 5/2010 | Haubrich et al. |
| 2010/0114143 A1 | 5/2010 | Albrecht et al. |
| 2010/0122995 A1 | 5/2010 | Thomas et al. |
| 2010/0171368 A1 | 7/2010 | Schatz et al. |
| 2010/0184371 A1 | 7/2010 | Cook et al. |
| 2010/0194334 A1 | 8/2010 | Kirby et al. |
| 2010/0210233 A1 | 8/2010 | Cook et al. |
| 2010/0211134 A1 | 8/2010 | Forsell |
| 2010/0222848 A1 | 9/2010 | Forsell |
| 2010/0222849 A1 | 9/2010 | Forsell |
| 2010/0225174 A1 | 9/2010 | Jiang |
| 2010/0244576 A1 | 9/2010 | Hillan et al. |
| 2010/0253340 A1 | 10/2010 | Corum et al. |
| 2010/0256708 A1 | 10/2010 | Thornton et al. |
| 2010/0277121 A1 | 11/2010 | Hall et al. |
| 2010/0305663 A1 | 12/2010 | Aghassian |
| 2010/0308939 A1 | 12/2010 | Kurs |
| 2010/0314946 A1 | 12/2010 | Budde et al. |
| 2010/0331919 A1 | 12/2010 | Digiore et al. |
| 2011/0025132 A1 | 2/2011 | Sato |
| 2011/0043050 A1 | 2/2011 | Yabe et al. |
| 2011/0046699 A1 | 2/2011 | Mazanec |
| 2011/0057607 A1 | 3/2011 | Carobolante |
| 2011/0101790 A1 | 5/2011 | Budgett |
| 2011/0109263 A1 | 5/2011 | Sakoda et al. |
| 2011/0115431 A1 | 5/2011 | Dunworth et al. |
| 2011/0127848 A1 | 6/2011 | Ryu et al. |
| 2011/0148215 A1 | 6/2011 | Marzetta et al. |
| 2011/0178361 A1 | 7/2011 | Yomtov |
| 2011/0181235 A1 | 7/2011 | Walley et al. |
| 2011/0205083 A1 | 8/2011 | Janna et al. |
| 2011/0234155 A1 | 9/2011 | Chen et al. |
| 2011/0241436 A1 | 10/2011 | Furukawa |
| 2011/0245892 A1 | 10/2011 | Kast et al. |
| 2011/0266880 A1 | 11/2011 | Kim et al. |
| 2011/0276110 A1 | 11/2011 | Whitehurst et al. |
| 2011/0278948 A1 | 11/2011 | Forsell |
| 2011/0291489 A1 | 12/2011 | Tsai et al. |
| 2011/0291613 A1 | 12/2011 | Rosik et al. |
| 2011/0295345 A1 | 12/2011 | Wells et al. |
| 2011/0298294 A1 | 12/2011 | Takada et al. |
| 2011/0301667 A1 | 12/2011 | Olson et al. |
| 2011/0313238 A1 | 12/2011 | Reichenbach et al. |
| 2012/0001485 A1 | 1/2012 | Uchida |
| 2012/0004709 A1 | 1/2012 | Chen |
| 2012/0032522 A1 | 2/2012 | Schatz et al. |
| 2012/0039102 A1 | 2/2012 | Shinoda |
| 2012/0057322 A1 | 3/2012 | Waffenschmidt |
| 2012/0065458 A1 | 3/2012 | Tol |
| 2012/0080957 A1 | 4/2012 | Cooper et al. |
| 2012/0091951 A1 | 4/2012 | Sohn |
| 2012/0104997 A1 | 5/2012 | Carobolante |
| 2012/0109256 A1 | 5/2012 | Meskins et al. |
| 2012/0119914 A1 | 5/2012 | Uchida |
| 2012/0146575 A1 | 6/2012 | Armstrong et al. |
| 2012/0149229 A1 | 6/2012 | Kearsley et al. |
| 2012/0150259 A1 | 6/2012 | Meskens |
| 2012/0153739 A1 | 6/2012 | Cooper et al. |
| 2012/0153954 A1 | 6/2012 | Ota et al. |
| 2012/0157753 A1 | 6/2012 | D'Ambrosio |
| 2012/0157754 A1 | 6/2012 | D'Ambrosio |
| 2012/0158407 A1 | 6/2012 | Forsell |
| 2012/0161539 A1 | 6/2012 | Kim et al. |
| 2012/0164943 A1 | 6/2012 | Bennett |
| 2012/0169132 A1 | 7/2012 | Choudhary et al. |
| 2012/0169133 A1 | 7/2012 | Lisi et al. |
| 2012/0169137 A1 | 7/2012 | Lisi et al. |
| 2012/0169139 A1 | 7/2012 | Kudo |
| 2012/0169278 A1 | 7/2012 | Choi et al. |
| 2012/0175967 A1 | 7/2012 | Dibben et al. |
| 2012/0223592 A1* | 9/2012 | Kamata ............... H02J 7/025 307/104 |
| 2012/0235364 A1 | 9/2012 | Wang et al. |
| 2012/0239118 A1 | 9/2012 | Ozawa et al. |
| 2012/0245649 A1 | 9/2012 | Bohori et al. |
| 2012/0245664 A1 | 9/2012 | Smith et al. |
| 2012/0259398 A1 | 10/2012 | Chen et al. |
| 2012/0274148 A1 | 11/2012 | Sung et al. |
| 2012/0306433 A1 | 12/2012 | Kim et al. |
| 2013/0007949 A1 | 1/2013 | Kurs et al. |
| 2013/0060103 A1 | 3/2013 | Bergida et al. |
| 2013/0119773 A1 | 5/2013 | Davis |
| 2013/0123881 A1* | 5/2013 | Aghassian ......... A61N 1/37247 607/61 |
| 2013/0127253 A1 | 5/2013 | Stark et al. |
| 2013/0149960 A1 | 6/2013 | Dec et al. |
| 2013/0159956 A1 | 6/2013 | Verghese et al. |
| 2013/0190551 A1 | 7/2013 | Callaway et al. |
| 2013/0197607 A1 | 8/2013 | Wilder et al. |
| 2013/0214731 A1 | 8/2013 | Dinsmoor |
| 2013/0241306 A1 | 9/2013 | Aber et al. |
| 2013/0241468 A1 | 9/2013 | Moshfeghi |
| 2013/0249479 A1 | 9/2013 | Partovi |

(56) References Cited

U.S. PATENT DOCUMENTS

| | | |
|---|---|---|
| 2013/0271088 A1 | 10/2013 | Hwang et al. |
| 2013/0289334 A1 | 10/2013 | Badstibner et al. |
| 2013/0310630 A1 | 11/2013 | Smith et al. |
| 2013/0320773 A1 | 12/2013 | Schatz et al. |
| 2013/0331638 A1 | 12/2013 | Cameron et al. |
| 2014/0005466 A1 | 1/2014 | Crosby et al. |
| 2014/0011447 A1 | 1/2014 | Konanur et al. |
| 2014/0028110 A1 | 1/2014 | Petersen et al. |
| 2014/0028111 A1 | 1/2014 | Hansen et al. |
| 2014/0031606 A1 | 1/2014 | Hansen et al. |
| 2014/0152252 A1 | 6/2014 | Wood |
| 2014/0163644 A1 | 6/2014 | Scott et al. |
| 2014/0191709 A1 | 7/2014 | Celentano |
| 2014/0192934 A1* | 7/2014 | Ciacci ............... H04B 1/0003 375/329 |
| 2014/0265620 A1 | 9/2014 | Hoarau et al. |
| 2014/0265621 A1 | 9/2014 | Wong et al. |
| 2014/0275727 A1* | 9/2014 | Bonde ............... A61M 1/1086 600/17 |
| 2015/0123654 A1 | 5/2015 | Gagnon et al. |
| 2015/0207330 A1 | 7/2015 | Petersen |
| 2015/0207331 A1 | 7/2015 | Petersen |
| 2015/0222127 A1 | 8/2015 | Hansen |
| 2015/0222128 A1 | 8/2015 | Hansen |
| 2015/0222139 A1 | 8/2015 | Petersen et al. |
| 2015/0229289 A1 | 8/2015 | Suzuki |
| 2015/0290373 A1 | 10/2015 | Rudser et al. |
| 2016/0135684 A1 | 5/2016 | Kappel et al. |
| 2016/0218432 A1 | 7/2016 | Pope et al. |
| 2016/0250484 A1 | 9/2016 | Nguyen et al. |
| 2016/0254704 A1 | 9/2016 | Hansen et al. |

FOREIGN PATENT DOCUMENTS

| | | |
|---|---|---|
| EP | 0589608 A2 | 9/1993 |
| EP | 1513241 A1 | 3/2005 |
| EP | 2267864 A2 | 6/2010 |
| GB | 2477034 A | 7/2011 |
| JP | H03109063 A | 5/1991 |
| JP | 11-506646 | 6/1999 |
| JP | 2001-513679 A | 9/2001 |
| JP | 2011-019291 A | 1/2011 |
| JP | 2012-154222 A | 8/2012 |
| JP | 2012-196031 A | 10/2012 |
| JP | 2013094456 A | 5/2013 |
| JP | 2013161640 A | 8/2013 |
| JP | 2014160611 A | 9/2014 |
| KR | 1020020089605 | 11/2002 |
| KR | 1020120007296 | 1/2012 |
| KR | 1020120077448 | 7/2012 |
| WO | 0001442 A2 | 1/2000 |
| WO | 74747 A1 | 12/2000 |
| WO | 137926 A1 | 5/2001 |
| WO | 2005106901 A2 | 11/2005 |
| WO | 2007053881 A1 | 5/2007 |
| WO | 2008066941 A2 | 6/2008 |
| WO | 2009018271 A1 | 2/2009 |
| WO | 2009021220 A1 | 2/2009 |
| WO | 2009023905 A1 | 2/2009 |
| WO | 2009042977 A1 | 4/2009 |
| WO | 2010030378 A1 | 3/2010 |
| WO | 2010089354 A2 | 8/2010 |
| WO | 2011081626 A1 | 7/2011 |
| WO | 2011113934 A1 | 9/2011 |
| WO | 2012002063 A1 | 1/2012 |
| WO | 2012056365 A2 | 5/2012 |
| WO | 2012087807 A2 | 6/2012 |
| WO | 2012087811 A2 | 6/2012 |
| WO | 2012087816 A2 | 6/2012 |
| WO | 2012087819 A2 | 6/2012 |
| WO | 2012099965 A2 | 7/2012 |
| WO | 2012141752 A2 | 10/2012 |
| WO | 2013110602 A1 | 8/2013 |
| WO | 2013138451 A1 | 9/2013 |
| WO | 2014039673 A1 | 3/2014 |
| WO | 2015070200 A1 | 5/2015 |

OTHER PUBLICATIONS

Chargepoint, Inc.; −chargepoin+®; product brochure; 4 pgs.; © 2014; retrieved Mar. 12, 2014 from the internet: http://www.chargepoint.com/network/.

Dixon, Jr.; Eddy current losses in transformer windings and circuit wiring; Unitrode Corp. Seminar Manual (SEM600) Watertown, MA; 12 pgs.; 1988 (year of pub. sufficiently earlier than effective US filing date and any foreign priority date).

Evatran; PluglessTM Level 2 EV Charging System (3.3kW); product brochure; 7 pgs.; retrieved Mar. 12, 2014 from the internet: http://www.pluglesspower.com/tech-specs/.

Ferret, B.; Electric vehicles get big boost!; Renewable Energy World; 3 pgs.; Jul. 30, 2012; retrieved Jul. 30, 2012 from the internet: http://www.renewableenergyworld.com/rea/blog/post/2012/07/.

Motavalli, Jim; WiTricity Takes Its Car-Charging Technology Out for a Road Test; New York Times; 3 pgs.; Jul. 25, 2012; retrieved Mar. 12, 2014 from the internet: http://wheels.blogs.nytimes.com/2012/07/25/witricity-takes-its-car-charging-technology-out-for-a-road-test/.

Notification of Transmittal of the International Search Report and the Written Opinion of the International Searching Authority for PCT Application No. PCT/US2015/051474, dated Dec. 30, 2015.

Development and Implementation of RFID Technology, Ed. Cristina Turcu, Feb. 2009, pp. 28-30, 93-97.

Merli, Francesco, et al., "Design, Realization and Measurements of a Miniature Antenna for Implantable Wireless Communication Systems", IEEE Transaction on Antennas and Propagation, vol. 59, No. 10, Oct. 2011, pp. 3544-3555.

Merli, Francesco, et al.,"The Effect of Insulating Layers on the Performance of Implanted Antennas", IEEE Transaction on Antennas and Propagation, vol. 59, No. 1, Jan. 2011, pp. 21-31.

Abadia, Javier, et al., 3D-Spiral Small Antenna Design and Realization for Biomdical Telemetry in the MICS Band. Radioengineering, vol. 18, No. 4, Dec. 2009, pp. 359-367.

International Search Report and Written Opinion in PCT/2014/064951 dated Feb. 13, 2015.

\* cited by examiner $$k \approx \frac{A_2}{A_1}$$

$$k \approx \frac{A_2}{A_1} \cos\theta$$

RESONANT POWER TRANSFER SYSTEMS WITH COMMUNICATIONS

CROSS-REFERENCE TO RELATED APPLICATIONS

This application is continuation of U.S. Nonprovisional application Ser. No. 15/032,290, filed Apr. 26, 2016, which is a National Stage application of PCT Application Serial No. PCT/US2014/064951, filed Nov. 11, 2014, which claims the benefit of U.S. Provisional Application No. 61/902,692, filed Nov. 11, 2013, titled "Resonant Power Transfer Systems with Communications", the entire contents and disclosures of which are incorporated herein by reference in their entirety.

INCORPORATION BY REFERENCE

All publications and patent applications mentioned in this specification are herein incorporated by reference to the same extent as if each individual publication or patent application was specifically and individually indicated to be incorporated by reference.

FIELD

The field relates generally to resonant wireless power transfer systems, and more specifically to implantable resonant wireless power transfer systems.

BACKGROUND

Many types of devices require transmitting energy between locations. Recent advances have accelerated the pace of innovation for wireless energy transmission (WET) without the use of cords. An example of a system using wireless energy technology is a powered, implantable medical device.

Many implantable medical devices require electrical systems to power the implant. Typically, this is achieved using percutaneous wiring to connect a power source to the implant. More recently, there has been interest in development of Transcutaneous Energy Transfer (TET) systems, e.g., through an oscillating magnetic field, for powering implantable medical devices.

A TET system usually includes a number of components or systems. A conventional TET system is implemented with a transmitting coil and a receiving coil for transmitting energy across the skin layer. The system typically includes a controller for driving the transmitting coil and/or controlling the implanted electronics.

Typically, implantable medical devices, such as implanted sensors, require very little power to operate. With such low power levels (on the order of milliwatts), power transfer levels and efficiency can be lower. With higher power devices (e.g., on the order of watts and up to 15 W or more), efficient transfer of wireless power is extremely important. Additionally, positions within the body are limited that can accommodate larger implanted devices, some of which are deep below the skin surface. These implant locations require additional attention to position and orientation of both the transmit and receive coils, as well as techniques to improve and maximize transfer efficiency.

Previous TET systems for implantable medical devices required the implanted receiver coil to be positioned just under the skin, and typically include a mechanical feature to align the receive and transmit coils and keep them together. By implanting these devices directly under the skin, the size and power requirements of these implanted devices is limited if they are to be powered by a TET system. TET systems can be designed for operation even while power is not being received by the receiver coil. In a typical configuration, solid-state electronics and a battery can power the implanted medical device when external power is interrupted or not available. In this case, it may be beneficial to provide a user interface or other electronic device to communicate information to the patient and/or caregiver regarding the implanted components. For example, a user interface may include alarms to notify the patient when the internal battery level is low.

Reliable communication between an implantable medical device, a user interface, and an external transmitter can be a challenge because of varying conditions and distances between the components of the TET system.

Radio signals have limitations when used for communication between implantable devices. Attenuation of radio signals by the human body is very large and can disrupt communication signals. Even under optimal circumstances, such as a shallow implant depth, a properly designed antenna, proper orientation of the implanted module, and a reliable radio link, attenuation can be on the order of 10 dB to 20 dB. For deeper implant depths, or if the implant rotates significantly from its intended position, attenuation may grow to 100 dB or more. This can lead to an unreliable or totally interrupted radio link with a high loss rate.

In-band communication has been used in implanted systems and comprises modulation of a receiver load that can be sensed by a transmitter. The problem with in-band communication is that it requires additional electronics in the resonant circuit, which lowers the power transfer efficiency and leads to additional heating of the receiver. Additionally, there is a fundamental design conflict between optimizing a resonant circuit to be power efficient and to transmit a meaningful amount of information. The former requires coils with a high quality factor while the latter prefers lower quality factors.

It is therefore desirable to provide a system in which the implant can communicate effectively with the user interface in the absence of the transmitter.

SUMMARY

A wireless power transfer system is provided comprising an external transmit resonator configured to transmit wireless power, an implantable receive resonator configured to receive the transmitted wireless power from the transmit resonator, and a user interface device comprising a resonant coil circuit, the resonant coil circuit being configured to receive magnetic communication signals from the transmit resonator or the receive resonator and to display information relating to the magnetic communication signals to a user of the user interface device.

In some embodiments, the user interface device is further configured to receive wireless power from the external transmit resonator.

In one embodiment, the resonant coil circuit of the user interface device is also configured to transmit magnetic communication signals to the transmit resonator or the receive resonator.

A wireless power transfer system is also provided, comprising an external transmit resonator configured to transmit wireless power, an implantable receive resonator configured to receive the transmitted wireless power from the transmit resonator, the receive resonator further comprising an ultrasound transceiver configured to transmit ultrasound communication signals, and a user interface device comprising an ultrasound transceiver configured to receive the ultrasound communication signals from the receive resonator and to display information relating to the ultrasound communication signals to a user of the TET system.

A method of transmitting wireless power and communications is provided, comprising transmitting wireless power from an external transmit resonator to an implanted receive resonator or an external user interface device, receiving wireless power with the implanted receive resonator or the external user interface device, transmitting magnetic communications from one of the transmit resonator, receive resonator, or user interface device, and receiving the magnetic communications with one of the transmit resonator, receive resonator, or user interface device.

A method of transmitting wireless power and communications is also provided, comprising transmitting wireless power from an external transmit resonator to an implanted receive resonator or an external user interface device, receiving wireless power with the implanted receive resonator or the external user interface device, transmitting ultrasonic communications from one of the transmit resonator, receive resonator, or user interface device, and receiving the ultrasonic communications with one of the transmit resonator, receive resonator, or user interface device.

A wireless energy transmission system is provided, comprising a transmit resonator configured to transmit wireless power, a receive resonator remote from the transmit resonator and configured to receive the transmitted wireless power from the transmit resonator, and a display device comprising a resonant coil circuit, the resonant coil circuit being configured to transmit or receive magnetic communication signals from the transmit resonator or the receive resonator and to display information relating to the magnetic communication signals to a user of the display device.

In some embodiments, the display device is wearable. In one embodiment, the display device is affixed to a wrist strap. In another embodiment, the display device is affixed to a belt.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
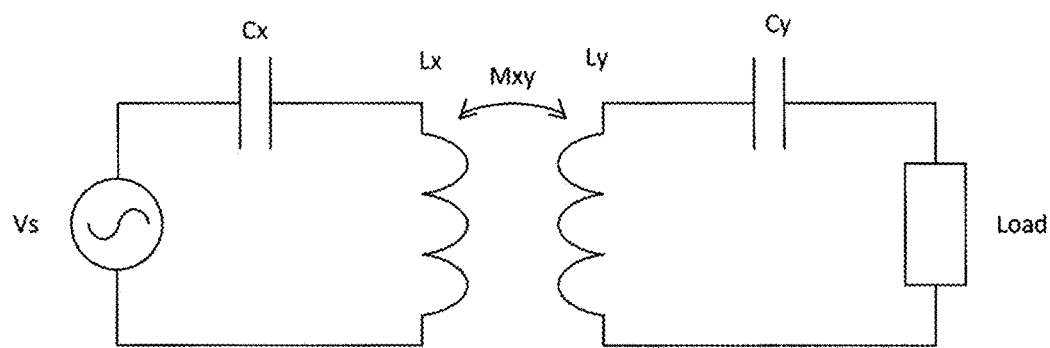
FIG. 1 illustrates a basic wireless power transfer system.

In the description that follows, like components have been given the same reference numerals, regardless of whether they are shown in different embodiments. To illustrate an embodiment(s) of the present disclosure in a clear and concise manner, the drawings may not necessarily be to scale and certain features may be shown in somewhat schematic form. Features that are described and/or illustrated with respect to one embodiment may be used in the same way or in a similar way in one or more other embodiments and/or in combination with or instead of the features of the other embodiments.

Various aspects of the invention are similar to those described in International Patent Pub. No. WO2012045050; U.S. Pat. Nos. 8,140,168; 7,865,245; 7,774,069; 7,711,433; 7,650,187; 7,571,007; 7,741,734; 7,825,543; 6,591,139; 6,553,263; and 5,350,413; and U.S. Pub. Nos. 2010/0308939; 2008/027293; and 2010/0102639, the entire contents of which patents and applications are incorporated herein for all purposes.

Wireless Power Transmission System

Power may be transmitted wirelessly by magnetic induction. In various embodiments, the transmitter and receiver are closely coupled.

In some cases "closely coupled" or "close coupling" refers to a system that requires the coils to be very near each other in order to operate. In some cases "loosely coupled" or "loose coupling" refers to a system configured to operate when the coils have a significant spatial and/or axial separation, and in some cases up to distance equal to or less than the diameter of the larger of the coils. In some cases, "loosely coupled" or "loose coupling" refers a system that is relatively insensitive to changes in physical separation and/or orientation of the receiver and transmitter.

In various embodiments, the transmitter and receiver are non-resonant coils. For example, a change in current in one coil induces a changing magnetic field. The second coil within the magnetic field picks up the magnetic flux, which in turn induces a current in the second coil. An example of a closely coupled system with non-resonant coils is described in International Pub. No. WO2000/074747, incorporated herein for all purposes by reference. A conventional transformer is another example of a closely coupled, non-resonant system. In various embodiments, the transmitter and receiver are resonant coils. For example, one or both of the coils is connected to a tuning capacitor or other means for controlling the frequency in the respective coil. An example of closely coupled system with resonant coils is described in International Pub. Nos. WO2001/037926; WO2012/087807; WO2012/087811; WO2012/087816; WO2012/087819; WO2010/030378; and WO2012/056365, and U.S. Pub. No. 2003/0171792, incorporated herein for all purposes by reference.

In various embodiments, the transmitter and receiver are loosely coupled. For example, the transmitter can resonate to propagate magnetic flux that is picked up by the receiver at relatively great distances. In some cases energy can be transmitted over several meters. In a loosely coupled system power transfer may not necessarily depend on a critical distance. Rather, the system may be able to accommodate changes to the coupling coefficient between the transmitter and receiver. An example of a loosely coupled system is described in International Pub. No. WO2012/045050, incorporated herein for all purposes by reference.

Power may be transmitted wirelessly by radiating energy. In various embodiments, the system comprises antennas. The antennas may be resonant or non-resonant. For example, non-resonant antennas may radiate electromagnetic waves to create a field. The field can be near field or far field. The field can be directional. Generally far field has greater range but a lower power transfer rate. An example of such a system for radiating energy with resonators is described in International Pub. No. WO2010/089354, incorporated herein for all purposes by reference. An example of such a non-resonant system is described in International Pub. No. WO2009/018271, incorporated herein for all purposes by reference. Instead of antenna, the system may comprise a high energy light source such as a laser. The system can be configured so photons carry electromagnetic energy in a spatially restricted, direct, coherent path from a transmission point to a receiving point. An example of such a system is described in International Pub. No. WO2010/089354, incorporated herein for all purposes by reference.

Power may also be transmitted by taking advantage of the material or medium through which the energy passes. For example, volume conduction involves transmitting electrical energy through tissue between a transmitting point and a receiving point. An example of such a system is described in International Pub. No. WO2008/066941, incorporated herein for all purposes by reference.

Power may also be transferred using a capacitor charging technique. The system can be resonant or non-resonant. Exemplars of capacitor charging for wireless energy transfer are described in International Pub. No. WO2012/056365, incorporated herein for all purposes by reference.

The system in accordance with various aspects of the invention will now be described in connection with a system for wireless energy transfer by magnetic induction. The exemplary system utilizes resonant power transfer. The system works by transmitting power between the two inductively coupled coils. In contrast to a transformer, however, the exemplary coils are not coupled together closely. A transformer generally requires the coils to be aligned and positioned directly adjacent each other. The exemplary system accommodates looser coupling of the coils.

While described in terms of one receiver coil and one transmitter coil, one will appreciate from the description herein that the system may use two or more receiver coils and two or more transmitter coils. For example, the transmitter may be configured with two coils—a first coil to resonate flux and a second coil to excite the first coil. One will further appreciate from the description herein that usage of "resonator" and "coil" may be used somewhat interchangeably. In various respects, "resonator" refers to a coil and a capacitor connected together.

In accordance with various embodiments of this disclosure, the system comprises one or more transmitters configured to transmit power wirelessly to one or more receivers. In various embodiments, the system includes a transmitter and more than one receiver in a multiplexed arrangement. A frequency generator may be electrically coupled to the transmitter to drive the transmitter to transmit power at a particular frequency or range of frequencies. The frequency generator can include a voltage controlled oscillator and one or more switchable arrays of capacitors, a voltage controlled oscillator and one or more varactors, a phase-locked-loop, a direct digital synthesizer, or combinations thereof. The transmitter can be configured to transmit power at multiple frequencies simultaneously. The frequency generator can include two or more phase-locked-loops electrically coupled to a common reference oscillator, two or more independent voltage controlled oscillators, or combinations thereof. The transmitter can be arranged to simultaneously delivery power to multiple receivers at a common frequency.

In various embodiments, the transmitter is configured to transmit a low power signal at a particular frequency. The transmitter may transmit the low power signal for a particular time and/or interval. In various embodiments, the transmitter is configured to transmit a high power signal wirelessly at a particular frequency. The transmitter may transmit the high power signal for a particular time and/or interval.

In various embodiments, the receiver includes a frequency selection mechanism electrically coupled to the receiver coil and arranged to allow the resonator to change a frequency or a range of frequencies that the receiver can receive. The frequency selection mechanism can include a switchable array of discrete capacitors, a variable capacitance, one or more inductors electrically coupled to the receiving antenna, additional turns of a coil of the receiving antenna, or combinations thereof.

In general, most of the flux from the transmitter coil does not reach the receiver coil. The amount of flux generated by the transmitter coil that reaches the receiver coil is described by "k" and referred to as the "coupling coefficient."

In various embodiments, the system is configured to maintain a value of k in the range of between about 0.2 to about 0.01. In various embodiments, the system is configured to maintain a value of k of at least 0.01, at least 0.02, at least 0.03, at least 0.04, or at least 0.05.

In various embodiments, the coils are physically separated. In various embodiments, the separation is greater than a thickness of the receiver coil. In various embodiments, the separation distance is equal to or less than the diameter of the larger of the receiver and transmitter coil.

Because most of the flux does not reach the receiver, the transmitter coil must generate a much larger field than what is coupled to the receiver. In various embodiments, this is accomplished by configuring the transmitter with a large number of amp-turns in the coil.

Since only the flux coupled to the receiver gets coupled to a real load, most of the energy in the field is reactive. The current in the coil can be sustained with a capacitor connected to the coil to create a resonator. The power source thus only needs to supply the energy absorbed by the receiver. The resonant capacitor maintains the excess flux that is not coupled to the receiver.

In various embodiments, the impedance of the receiver is matched to the transmitter. This allows efficient transfer of energy out of the receiver. In this case the receiver coil may not need to have a resonant capacitor.

Turning now to FIG. 1, a simplified circuit for wireless energy transmission is shown. The exemplary system shows a series connection, but the system can be connected as either series or parallel on either the transmitter or receiver side.

The exemplary transmitter includes a coil Lx connected to a power source Vs by a capacitor Cx. The exemplary receiver includes a coil Ly connected to a load by a capacitor Cy. Capacitor Cx may be configured to make Lx resonate at a desired frequency. Capacitance Cx of the transmitter coil may be defined by its geometry. Inductors Lx and Ly are connected by coupling coefficient k. Mxy is the mutual inductance between the two coils. The mutual inductance, Mxy, is related to coupling coefficient, k.

$$Mxy = k\sqrt{Lx \cdot Ly}$$

In the exemplary system the power source Vs is in series with the transmitter coil Lx so it may have to carry all the reactive current. This puts a larger burden on the current rating of the power source and any resistance in the source will add to losses.

The exemplary system includes a receiver configured to receive energy wirelessly transmitted by the transmitter. The exemplary receiver is connected to a load. The receiver and load may be connected electrically with a controllable switch.

In various embodiments, the receiver includes a circuit element configured to be connected or disconnected from the receiver coil by an electronically controllable switch. The electrical coupling can include both a serial and parallel arrangement. The circuit element can include a resistor, capacitor, inductor, lengths of an antenna structure, or combinations thereof. The system can be configured such that power is transmitted by the transmitter and can be received by the receiver in predetermined time increments.

In various embodiments, the transmitter coil and/or the receiver coil is a substantially two-dimensional structure. In various embodiments, the transmitter coil may be coupled to a transmitter impedance-matching structure. Similarly, the receiver coil may be coupled to a receiver impedance-matching structure. Examples of suitable impedance-matching structures include, but are not limited to, a coil, a loop, a transformer, and/or any impedance-matching network. An impedance-matching network may include inductors or capacitors configured to connect a signal source to the resonator structure.

In various embodiments, the transmitter is controlled by a controller (not shown) and driving circuit. The controller and/or driving circuit may include a directional coupler, a signal generator, and/or an amplifier. The controller may be configured to adjust the transmitter frequency or amplifier gain to compensate for changes to the coupling between the receiver and transmitter.

In various embodiments, the transmitter coil is connected to an impedance-matched coil loop. The loop is connected to a power source and is configured to excite the transmitter coil. The first coil loop may have finite output impedance. A signal generator output may be amplified and fed to the transmitter coil. In use power is transferred magnetically between the first coil loop and the main transmitter coil, which in turns transmits flux to the receiver. Energy received by the receiver coil is delivered by Ohmic connection to the load.

One of the challenges to a practical circuit is how to get energy in and out of the resonators. Simply putting the power source and load in series or parallel with the resonators is difficult because of the voltage and current required. In various embodiments, the system is configured to achieve an approximate energy balance by analyzing the system characteristics, estimating voltages and currents involved, and controlling circuit elements to deliver the power needed by the receiver.

In an exemplary embodiment, the system load power, $P_L$, is assumed to be 15 Watts and the operating frequency of the system, f, is 250 kHz. Then, for each cycle the load removes a certain amount of energy from the resonance:

$$e_L = \frac{P_L}{f} = 60 \ \mu J \text{ Energy the load removes in one cycle}$$

It has been found that the energy in the receiver resonance is typically several times larger than the energy removed by the load for operative, implantable medical devices. In various embodiments, the system assumes a ratio 7:1 for energy at the receiver versus the load removed. Under this assumption, the instantaneous energy in the exemplary receiver resonance is 420 µJ.

The exemplary circuit was analyzed and the self inductance of the receiver coil was found to be 60 uH. From the energy and the inductance, the voltage and current in the resonator could be calculated.

$$e_y = \frac{1}{2} L i^2$$

$$i_y = \sqrt{\frac{2 e_y}{L}} = 3.74 \text{ A peak}$$

$$v_y = \omega L_y i_y = 352 \text{ V peak}$$

The voltage and current can be traded off against each other. The inductor may couple the same amount of flux regardless of the number of turns. The Amp-turns of the coil needs to stay the same in this example, so more turns means the current is reduced. The coil voltage, however, will need to increase. Likewise, the voltage can be reduced at the expense of a higher current. The transmitter coil needs to have much more flux. The transmitter flux is related to the receiver flux by the coupling coefficient. Accordingly, the energy in the field from the transmitter coil is scaled by k.

$$e_x = \frac{e_y}{k}$$

Given that k is 0.05:

$$e_x = \frac{420 \ \mu J}{0.05} = 8.4 \text{ mJ}$$

For the same circuit the self inductance of the transmitter coil was 146 uH as mentioned above. This results in:

$$i_x = \sqrt{\frac{2 e_x}{L}} = 10.7 \text{ A peak}$$

$$v_x = \omega L_x i_x = 2460 \text{ V peak}$$

One can appreciate from this example, the competing factors and how to balance voltage, current, and inductance to suit the circumstance and achieve the desired outcome. Like the receiver, the voltage and current can be traded off against each other. In this example, the voltages and currents in the system are relatively high. One can adjust the tuning to lower the voltage and/or current at the receiver if the load is lower.

Estimation of Coupling Coefficient and Mutual Inductance

As explained above, the coupling coefficient, k, may be useful for a number of reasons. In one example, the coupling coefficient can be used to understand the arrangement of the coils relative to each other so tuning adjustments can be made to ensure adequate performance. If the receiver coil moves away from the transmitter coil, the mutual inductance will decrease, and ceteris paribus, less power will be transferred. In various embodiments, the system is configured to make tuning adjustments to compensate for the drop in coupling efficiency.

The exemplary system described above often has imperfect information. For various reasons as would be understood by one of skill in the art, the system does not collect data for all parameters. Moreover, because of the physical gap between coils and without an external means of communications between the two resonators, the transmitter may have information that the receiver does not have and vice versa. These limitations make it difficult to directly measure and derive the coupling coefficient, k, in real time.

Described below are several principles for estimating the coupling coefficient, k, for two coils of a given geometry. The approaches may make use of techniques such as Biot-Savart calculations or finite element methods. Certain assumptions and generalizations, based on how the coils interact in specific orientations, are made for the sake of simplicity of understanding. From an electric circuit point of view, all the physical geometry permutations can generally lead to the coupling coefficient.

Figure 2:
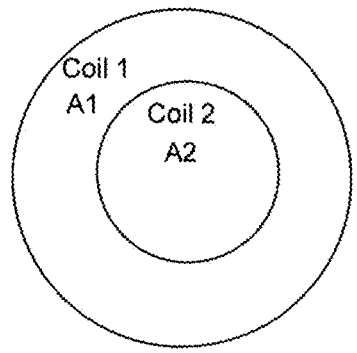
FIG. 2 illustrates the flux generated by a pair of coils.

If two coils are arranged so they are in the same plane, with one coil circumscribing the other, then the coupling coefficient can be estimated to be roughly proportional to the ratio of the area of the two coils. This assumes the flux generated by coil 1 is roughly uniform over the area it encloses as shown in FIG. 2.

Figure 3A:
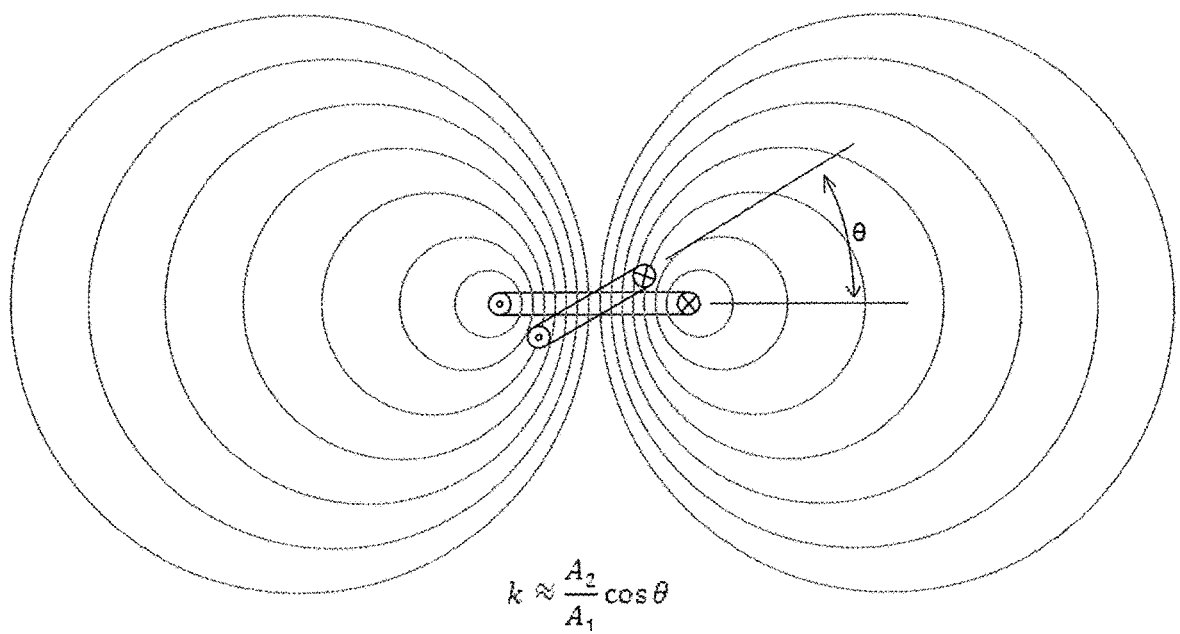
FIGS. 3A-3B illustrate the effect of coil alignment on the coupling coefficient.

If the coils are out of alignment such that the coils are at a relative angle, the coupling coefficient will decrease. The amount of the decrease is estimated to be about equal to the cosine of the angle as shown in FIG. 3A. If the coils are orthogonal to each other such that theta (θ) is 90 degrees, the flux will not be received by the receiver and the coupling coefficient will be zero.

Figure 3B:
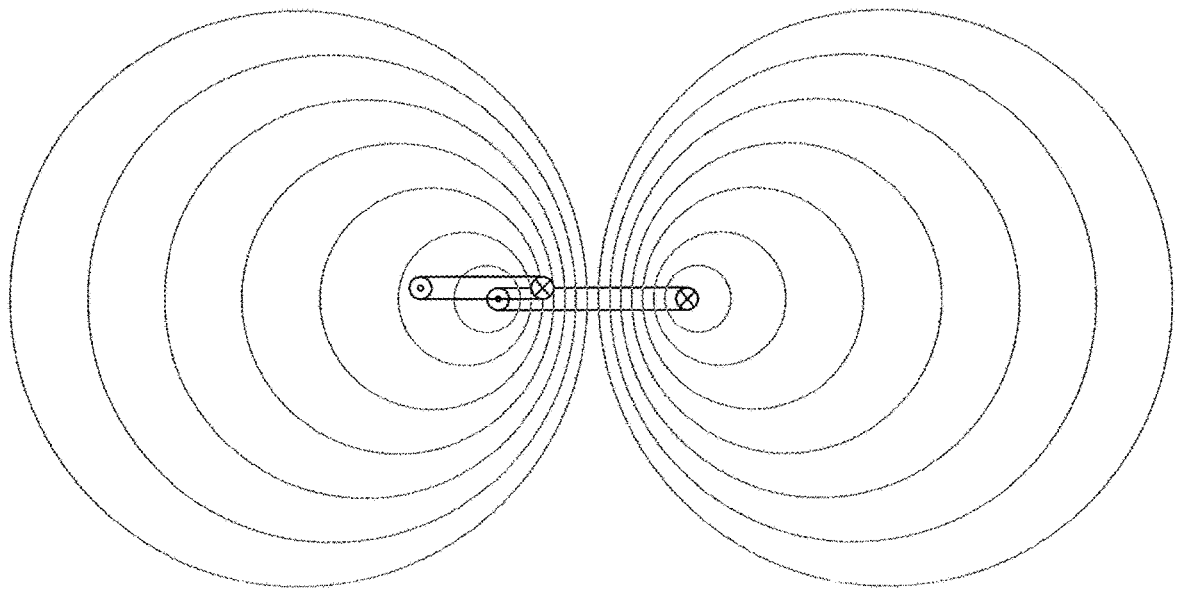

If the coils are arraigned such that half the flux from one coil is in one direction and the other half is in the other direction, the flux cancels out and the coupling coefficient is zero, as shown in FIG. 3B.

A final principle relies on symmetry of the coils. The coupling coefficient and mutual inductance from one coil to the other is assumed to be the same regardless of which coil is being energized.

$$M_{xy} = M_{yx}$$

Figure 4:
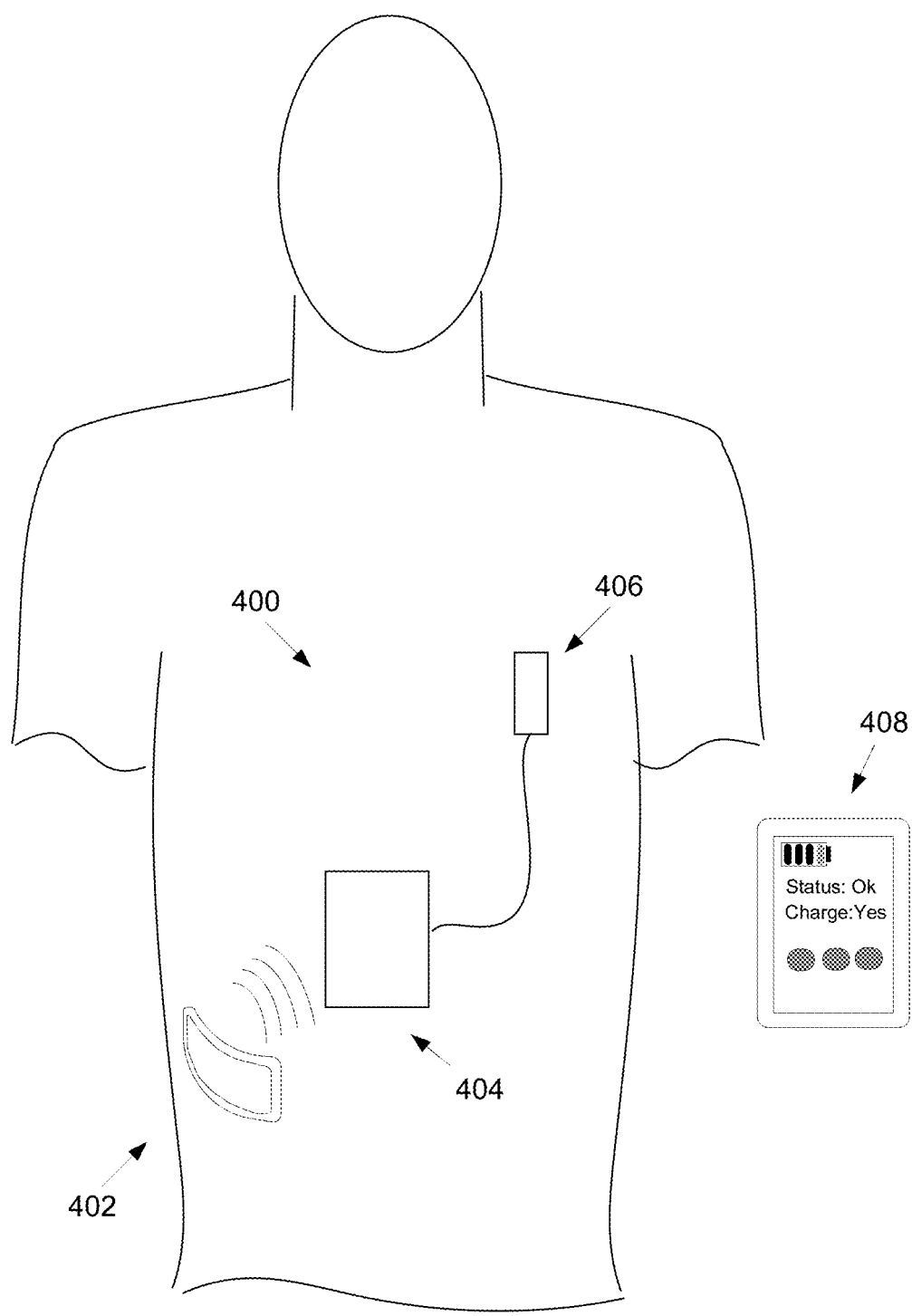
FIG. 4 shows one embodiment of a TET system including a resonator coil, a receiver, an implanted medical device, and a user interface.

FIG. 4 illustrates one embodiment of a TET system 400 including transmitter and resonator coil 402 positioned on an exterior portion of a patient. In FIG. 4, the transmitter can be either a flat resonator coil or a curved or conformable resonator coil configured to conform to the anatomy of the patient. The transmitter can be configured to transmit wireless energy to a receiver 404 implanted in the patient. In some embodiments, the receiver can be electrically coupled to an implanted medical device 406, such as a heart pump, to provide energy for the operation of the medical device.

The system 400 can further include a user interface 408 that can communicate with the receiver and/or transmitter. The user interface can be, for example, a handheld device such as a smartphone, tablet, or PC, or even a wearable device in the form factor of a wristwatch. In general, the user interface includes a display for conveying information to the patient and hardware configured to communicate wirelessly with the rest of the TET system. The user interface can display to a user, for example, operating status of the implant, battery life of the implant, charging status, or any other number of information or parameters relating to the implant or to the patient's health. The user interface may include and display alarms, such as low battery level, charging reminders, or a device malfunction (including information about malfunctions from either the implanted power receiver or the attached medical device). Communication from the receiver to either the user interface or the transmitter is wireless since it must pass through layers of human tissue. The wireless communication can be further complicated by the environment surrounding the patient (e.g., if the patient is swimming and submerged in water).

In some embodiments, the user interface 408 can include a resonant circuit. The resonant circuit can be configured with a high quality factor and be designed to not dissipate significant amounts of energy from the magnetic field. The resonant circuit in the user interface can contain electronics to carry out a variety of functions. For example, the user interface can communicate and receive information from the implanted receiver with the resonant circuits. The information can include data related to the operation of medical device 406. In one embodiment, the medical device 460 is a ventricular assist device (VAD) and the data communicated to the user interface includes power consumption, alarm event data, pump speed, pulsatility index, pump flow, system status, and the like.

The communication of information between the user interface and implanted components can be achieved by transmitting a magnetic signal to the receiver from the user interface, or alternatively transmitting a magnetic signal from the user interface to the receiver. In addition, the user interface could receive wireless power from the receiver or from the transmitter to recharge a power source in the user interface, much in the same manner in which the transmitter can recharge the implanted receiver. Since the communication is via magnetic signals within the resonant circuits, communications could be sent and received even if the patient was submerged in water. The use of magnetic resonance for communication also enables communication through layers of tissue with deep body implants.

In some embodiments, the user interface can include conventional radio communication hardware designed to communicate with the rest of the TET system via radio. In one embodiment, the resonant circuit is an adjunct to another communication system. In one embodiment, the resonant circuit is configured for communication as a back-up (e.g., if the primary communication system fails, such as the radio communication system). In other embodiments, the magnetic communication via resonant circuits can be the primary method of communication within the TET system.

Figure 5:
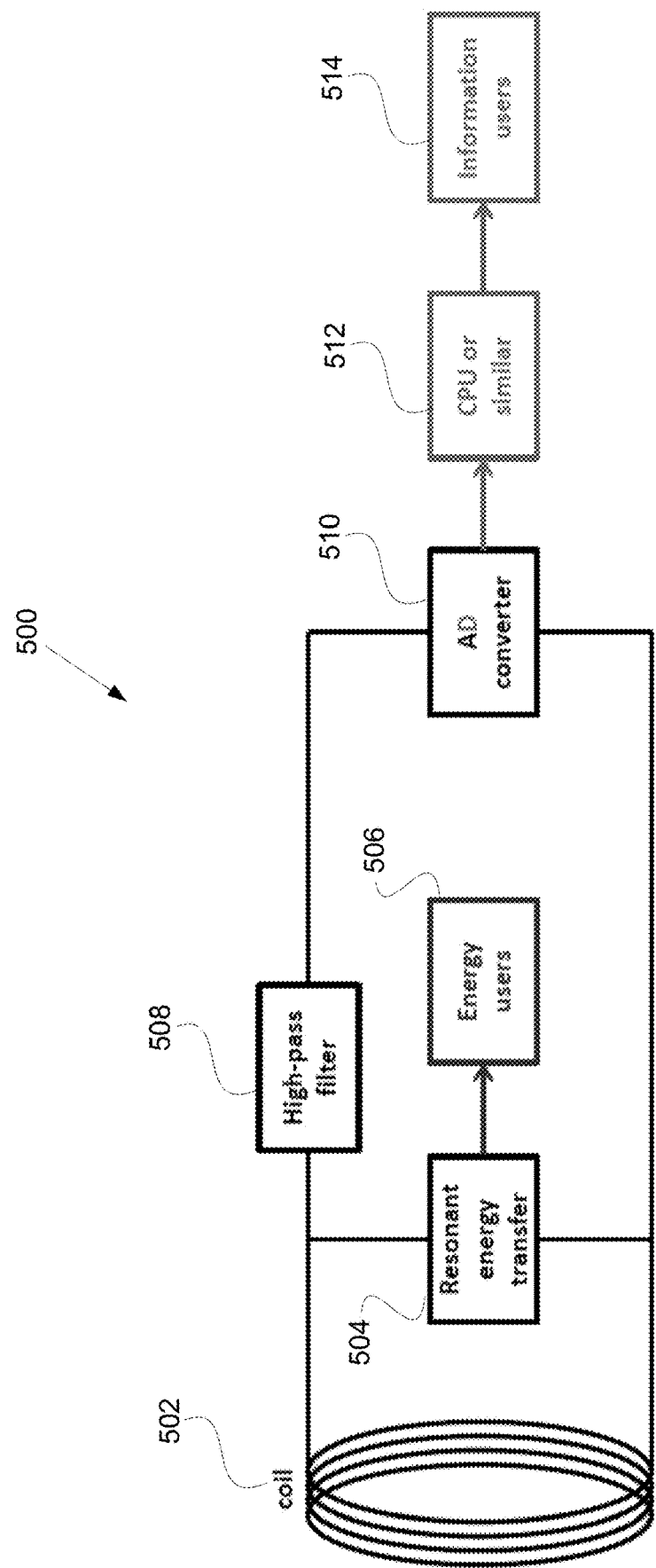
FIGS. 5-6 show reception and transmission of power and or communications in a receiver and transmitter.

FIG. 5 shows how a resonant circuit 500 including combined magnetic communications and magnetic energy transfer receiver might work. This can be, for example, the resonant circuit included in the user interface described above. The basic idea is that a coil 502 of the resonant circuit "picks up" (converts to a voltage) a magnetic field that contains both a large enough oscillation to transfer electric power/energy and an oscillation encoded to contain information. The quality factor of the resonant circuit must be chosen carefully; the quality factor should be high enough to efficiently transfer power/energy but low enough that a desired amount of information per unit time (bits/second) can be communicated. Information can be encoded either by amplitude modulation (AM), frequency modulation (FM), or a combination of both AM and FM. Quadrature modulation (or higher order modulation) can be used, and would be a natural choice if using an AM/FM combo.

The receiving coil in a TET system with only one receiver should be as large as possible, to maximize power efficiency and bit rate received. If there are multiple receivers in the system, the farthest receiver should be as large as possible. Nearer receivers may have smaller coils, depending on the desired power transfer efficiency.

As shown in FIG. 5, the output from coil 502 can be split to a resonant energy transfer system 504 for delivery to energy users 506, which can represent a battery charging and power delivery feature for the user interface. The output from the coil can also be delivered to an AD-converter 508 (via an optional high-pass filter 510). The high-pass filter can remove the lower frequencies of the resonant energy transfer system. This protects the AD-converter from high voltages and allows a very simple AD-converter to be used (such as a three-level 1/undefined/0 converter). Alternatives to the high-pass filter include a low-pass filter (if the resonant energy transfer operates at a higher frequency than the communications), any type of voltage transformer or voltage step-down component to protect the AD-converter, or just leaving out the high-pass filter altogether (if the AD-converter is rated to receive high voltages). If a filter is not used, the AD-converter cannot be a simple three-level (or similar) converter, but must provide a large dynamic range, and the CPU 512 will have to process the raw signal, through Fast Fourier Transform or similar. Regardless of whether a filter is used, the CPU 512 passes the communications information along to the information users 514, such as, for example, the user interface described above for displaying critical information about the implant to the patient.

The resonant circuit should, at a minimum, contain a capacitor that together with the coil 502 gives the circuit a desired resonance frequency. The circuit can contain another coil ("exciter" coil) or a voltage-dividing capacitor before the power is delivered to a load. The load may be a bridge of FETs, rectifying the voltage to DC, or an AC-AC converter, or the voltage could just go straight out to the various energy users 506 (components that need the energy such as a display, e.g., batteries that need charging, or a motor, etc.).

The resonant circuit can operate at the same frequency as the other components of the TET system (including the receiver and the transmitter) or can be an independent resonant circuit operating at its own, different frequency. The resonant circuit can also be simplified to provide only a communications capability and not a resonant energy transfer capability for the user interface.

The high-pass filter removes the lower frequency of the resonant energy transfer system. This protects the DA-converter from high voltages and allows a very simple DA-converter to be used (such as a three-level 1/undefined/0 converter). Alternatives to the high-pass filter includes a low-pass filter (if the resonant energy transfer operates at a higher frequency than the comms), any type of voltage transformer or voltage step-down component to protect the DA-converter, or just leaving out the high-pass filter altogether (if the DA-converter is rated to receive high voltages). If a filter is not used, the DA-converter cannot be a simple three-level (or similar) converter, but must provide a large dynamic range, and the CPU will have to process the raw signal, through Fast Fourier Transform or similar.

The CPU 512 can be any type of signal processor.

An advantage of the magnetic communication scheme described above is the ability to transfer power in addition to data. The provision of a resonant circuit enables the transmission of energy which would not be possible with conventional magnetic communication coils.

The systems described herein may be particularly advantageous for consumer electronics because it eliminates the need for separate data and power mediums. The single system can be used to power the electronic device and/or transmit desired data between two remote components.

Figure 6:
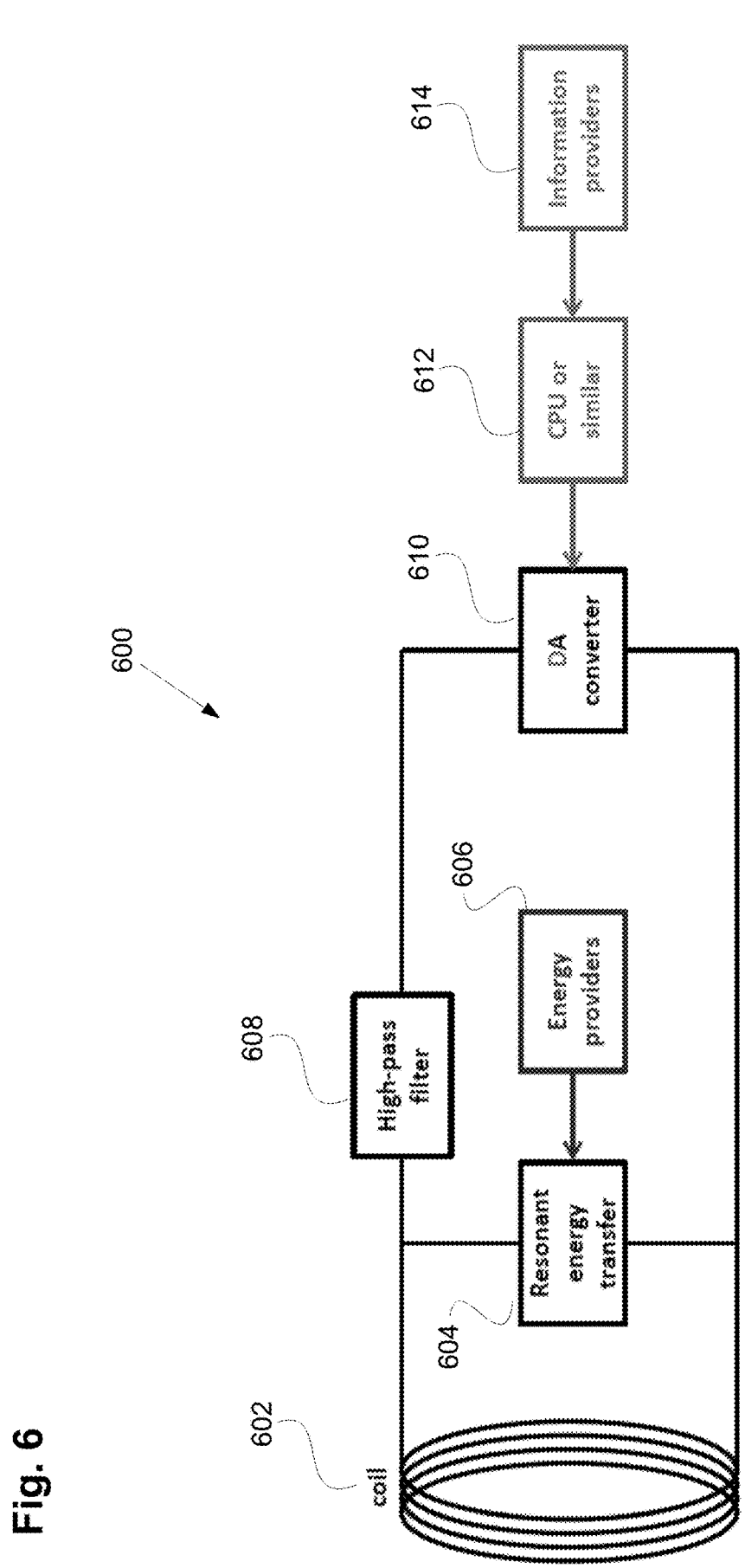

FIG. 6 illustrates how a resonant circuit 600 for a combined magnetic communications and magnetic energy transfer transmitter might work. Compared to the receiver illustrated in FIG. 5, information in the transmitter of FIG. 6 flows the other direction, from information providers 615 (e.g., sensors, or the user interface), to a signal processing CPU 612 or similar, to an AD-converter 610 (possibly with an amplifier), through a high-pass filter 608 to the coil. Energy can also flow the other direction from energy providers 606 (e.g., a battery pack and a FETs bridge) to the resonant energy transfer system 604.

In another embodiment, ultrasonic communication can be used between the components of the TET system in place of the magnetic communication described above. Ultrasonic transceivers can be included in the TETS transmitter, receiver, or user interface to send and transmit information via coded ultrasound signals. A decoder and encoder can further be coupled to each transceiver. Since attenuation of sound waves can be significantly lower than attenuation of radio signals in the human body, this method of communication can also be more reliable than standard radio communications.

A transceiver according to one embodiment can be split into two separate parts: a transducer that generates ultrasound signals and a microphone, transducer, or other receiver that receives the ultrasound signals. In some embodiments, ultrasound signals can be transmitted with a frequency ranging from approximately 100 kHz-20 MHz or higher. Generally, the lower the frequency, the less attenuated the signal gets during transmission and the longer the signal can travel while still being useful for communications. For example, at 20 MHz the attenuation depth is about 2 cm. Frequencies below 100 kHz can interfere with animal hearing, in particular pets that live with a patient.

Figure 7B:
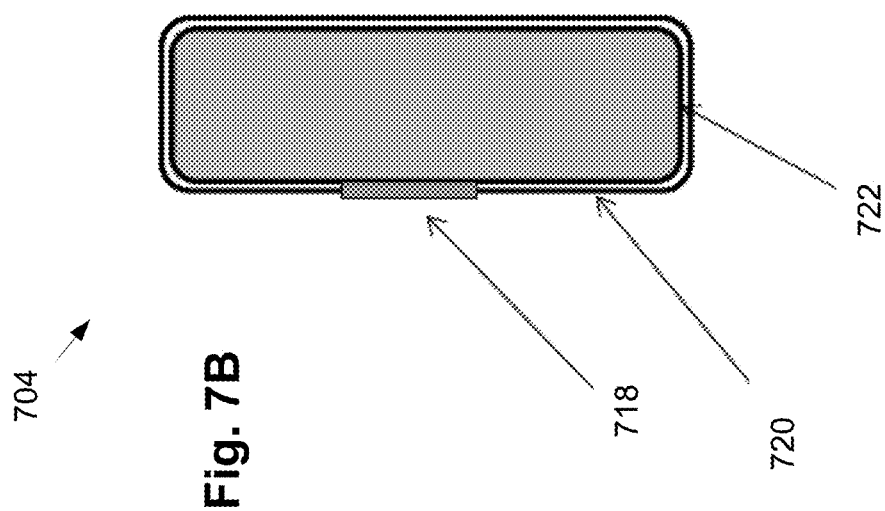
FIGS. 7A-7B show some embodiments of ultrasonic communications in a TET system.
Figure 7A:
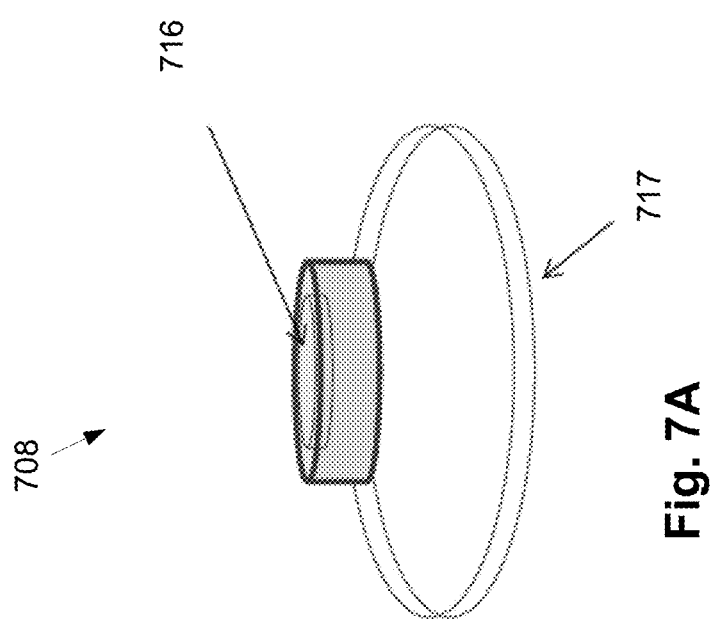

FIGS. 7A-7B illustrate embodiments of an ultrasonic communication system for use in a TET system, such as the TET system of FIG. 4. For example, the system shown in FIG. 7A can include a user interface 708, similar to the user interface 404 of FIG. 4. In some embodiments, the user interface can be worn by the user, such as on a wrist band 717. Alternatively, the user interface can be worn by the patient by attaching it to a belt, to adhesive, to Velcro, or integrating it on or within an article of clothing. FIG. 7B illustrates an implantable receiver 704, similar to the receiver 404 of FIG. 4. The user interface 708 can include an ultrasound transceiver 716 configured to communicate with an ultrasound transceiver 718 disposed on or in the receiver 704. In the illustrated example, the transceiver 718 can be disposed outside the ferrite layer 720 and titanium layer 722 that make up the housing of the implanted device.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims. Although described in some respects as a medical system, one will appreciate from the description herein that the principles can apply equally to other types of systems including, but not limited to, consumer electronics, automotive, phones and personal communication devices, gaming devices, and computers and peripherals.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A wireless power transfer system, comprising:
an external transmit resonator configured to transmit wireless power;
an implantable receive resonator configured to receive the transmitted wireless power from the external transmit resonator; and
a user interface device separate from the external transmit resonator and the implantable receive resonator, the user interface device comprising a resonant coil circuit, the resonant coil circuit configured to receive both magnetic communication signals and wireless power from the external transmit resonator or the implantable receive resonator and to display information relating to the magnetic communication signals to a user of the user interface device, the resonant coil circuit of the user interface device comprising:
a coil configured to simultaneously receive the magnetic communication signals and the wireless power, the coil coupled between a first node and a second node;
a resonant energy transfer system coupled to the coil and configured to deliver the wireless power from the coil to an energy user, the resonant energy transfer system coupled between the first node and the second node;
a signal processor configured to process the magnetic communication signals;
an AD-converter coupled between the coil and the signal processor, the AD-converter coupled between the first node and the second node; and
a high-pass filter coupled between the coil and the AD-converter, the high-pass filter further coupled between the first node and the AD-converter, the high-pass filter further coupled between the resonant energy transfer system and the AD-converter, the high-pass filter further coupled directly to the coil through the first node, wherein the high-pass filter is directly coupled to the resonant energy transfer system through the first node, and wherein the resonant energy transfer system is directly coupled to the AD-converter through the second node.

2. The system of claim 1 wherein the resonant coil circuit of the user interface device is also configured to transmit magnetic communication signals to the external transmit resonator or the implantable receive resonator.

3. The system of claim 1, wherein the user interface device is wearable.

4. The system of claim 3, wherein the user interface device is affixed to a wrist strap.

5. The system of claim 3, wherein the user interface device is affixed to a belt.

6. A method of transmitting wireless power and communications, comprising:
transmitting wireless power from at least one of an external transmit resonator and an implanted receive resonator to an external user interface device;
transmitting magnetic communication signals from at least one of the external transmit resonator and the implanted receive resonator to the external user interface device, wherein the external user interface device includes:
a coil configured to simultaneously receive the magnetic communication signals and the wireless power, the coil coupled between a first node and a second node;
a resonant energy transfer system coupled to the coil and configured to deliver the wireless power from the coil to an energy user, the resonant energy transfer system coupled between the first node and the second node;
a signal processor configured to process the magnetic communication signals; and
an AD-converter coupled between the coil and the signal processor, the AD-converter coupled between the first node and the second node;
a high-pass filter coupled between the coil and the AD-converter, the high-pass filter further coupled between the first node and the AD-converter, the high-pass filter further coupled between the resonant energy transfer system and the AD-converter, the high-pass filter further coupled directly to the coil through the first node, wherein the high-pass filter is directly coupled to the resonant energy transfer system through the first node, and wherein the resonant energy transfer system is directly coupled to the AD-converter through the second node; and
a display configured to display information relating to the magnetic communication signals;
receiving the wireless power with the external user interface device; and
receiving the magnetic communication signals with the external user interface device.

7. The method of claim 6, wherein the external user interface device is wearable.

8. The method of claim 7, wherein the external user interface device is affixed to a wrist strap.

9. The method of claim 7, wherein the external user interface device is affixed to a belt.

10. A wireless energy transmission system, comprising:
a transmit resonator configured to transmit wireless power;
a receive resonator remote from the transmit resonator and configured to receive the transmitted wireless power from the transmit resonator; and
a display device separate from the transmit resonator and receive resonator, the display device comprising a resonant coil circuit, the resonant coil circuit configured to transmit or receive magnetic communication signals and wireless power from the transmit resonator or the receive resonator and to display information relating to the magnetic communication signals to a user of the display device, the resonant coil circuit of the display device comprising:

a coil configured to simultaneously receive the magnetic communication signals and the wireless power, the coil coupled between a first node and a second node;

a resonant energy transfer system coupled to the coil and configured to deliver the wireless power from the coil to an energy user, the resonant energy transfer system coupled between the first node and the second node;

a signal processor configured to process the magnetic communication signals;

an AD-converter coupled between the coil and the signal processor, the AD-converter coupled between the first node and the second node; and a high-pass filter coupled between the coil and the AD-converter, the high-pass filter further coupled between the first node and the AD-converter, the high-pass filter further coupled between the resonant energy transfer system and the AD-converter, the high-pass filter further coupled directly to the coil through the first node, wherein the high-pass filter is directly coupled to the resonant energy transfer system through the first node, and wherein the resonant energy transfer system is directly coupled to the AD-converter through the second node.

11. The system of claim 10, wherein the display device is wearable.

12. The system of claim 11, wherein the display device is affixed to a wrist strap.

13. The system of claim 11, wherein the display device is affixed to a belt.

* * * * *